United States Patent [19]

Diem et al.

[11] 4,234,848
[45] Nov. 18, 1980

[54] TEST HEAD FOR INDUCTIVE SURFACE TESTING HAVING PLURAL RESONANT COILS HELD IN CONDUCTIVE HOLDER

[75] Inventors: Rudolf Diem, Dittelbrunn; Hans-Jürgen Hentrich, Schweinfurt, both of Fed. Rep. of Germany

[73] Assignee: SKF Kugellagerfabriken GmbH, Schweinfurt, Fed. Rep. of Germany

[21] Appl. No.: 908,929

[22] Filed: May 24, 1978

[30] Foreign Application Priority Data

Jun. 4, 1977 [DE] Fed. Rep. of Germany ....... 2725354

[51] Int. Cl.$^3$ ............................................. G01R 33/00
[52] U.S. Cl. .................................... 324/262; 324/237; 336/83
[58] Field of Search ............... 324/214, 220, 226, 228, 324/234, 236, 237–243, 262; 336/82, 83

[56] References Cited

U.S. PATENT DOCUMENTS

| | | | |
|---|---|---|---|
| 3,437,918 | 4/1969 | Arnelo | 324/238 |
| 3,931,571 | 1/1976 | Hocking et al. | 324/236 |
| 3,976,936 | 8/1976 | Nishino | 324/232 |

OTHER PUBLICATIONS

F. Verlag, "Telefunkin Laborbuch," vol. 1, pp. 142–145, Munich.

Primary Examiner—Gerard R. Strecker
Assistant Examiner—Walter E. Snow
Attorney, Agent, or Firm—Daniel M. Rosen

[57] ABSTRACT

A test head for the inductive surface testing of metallic workpieces is provided with eddy-current probes respectively disposed in a plurality of holes in a holder. Each eddy-current probe is part of an individual resonant circuit and formed of coil with a ferrite core, the axis of the coil extending substantially at right angles to the workpiece surface. The holder comprises an electrically or magnetically conductive material, thereby increasing the area over which the field of each said probe is effective.

7 Claims, 2 Drawing Figures

TEST HEAD FOR INDUCTIVE SURFACE TESTING HAVING PLURAL RESONANT COILS HELD IN CONDUCTIVE HOLDER

BACKGROUND OF THE INVENTION

The invention relates to testing apparatus and particularly to test heads for the inductive surface testing of metallic workpieces. Inductive test heads are conventionally provided with eddy-current probes disposed in holes in a holder, each eddy-current probe being part of an individual resonant circuit and being formed by a single- or multilayer coil having a ferrite core, the axis of the coil extending substantially at right angles to the surface of the workpiece.

DESCRIPTION OF THE PRIOR ART

A test head of the type mentioned is known wherein the surface of metallic pipes is tested by moving the pipe helically relative to the eddy-current probes and the test head back and forth parallel to the circumference of the pipe so that areal scanning of the surface takes place for the detection of longitudinal and transverse defects (cracks). An example of such a test head is shown in German Pat. No. 2,037,787. This prior art device has the drawback that complicated and sometimes troublesome drive elements must be provided to produce the reciprocating motion of the test head. Notwithstanding these drive elements, the ability of the prior-art test head to detect flaws, or to indicate sensitivity, respectively, leaves much to be desired since cracks extending in the direction, or nearly in the direction, of the line of contact of the individual point-shaped probes are not indicated at all or then only weakly.

It is therefore the object of the present invention to provide an improved eddy-current probe test head which has a large area indicating sensitivity for longitudinal and transverse defects and requires no drive for the reciprocating motion.

SUMMARY OF THE INVENTION

In accordance with the invention, the foregoing object is accomplished in that the holder for the eddy-current probes is made of an electrically and/or magnetically conducting material. Electromagnetic fields are thus produced in the holder which increase the resonant frequency of the resonant circuits of the individual eddy-current probes and which surprisingly help to make possible areal scanning of the workpiece surface. Thus, scanning results in which an indication-sensitive induction field of the point-shaped eddy-current probes is present at a strength between the probes which is nearly as full as that immediately surrounding the probes.

In accordance with a further characteristic of the invention, the ends of the ferrite cores facing the workpiece and the front of the holder which faces the workpiece are in a common plane. As a result of this arrangement, the ferrite cores in the holder may be disposed in the holder so as to be in close proximity to the workpiece surface for producing a strong indication-sensitive induction field. At the same time, the attenuating effect of the electrically and/or magnetically conducting material of which the holder is made prevents a troublesome indicating error attributable to the approaching and withdrawing movements of the workpiece surface, for example, due to defects in shape of the workpiece moved under the test head.

In accordance with still another characteristic of the invention, the holder has, in the vicinity of the probes, slotlike notches which extend at right angles to the workpiece. In accordance with additional characteristics of the invention, these notches extend in the direction of movement of the work-piece surface relative to the holder, and are adapted to merge with the hole which accommodates the eddy-current probe. These notches form an air gap which prevents eddy-current generation about the coils and attendant deleterious heating of the holder since the induction field of the coils is not short-circuited in the holder. Moreover, these notches cause the individual resonant circuits of the eddy-current probes to be partly decoupled electromagnetically, which has the effect of increasing the indicating sensitivity, particularly when the eddy-current probes are connected in a differential or comparator circuit.

In accordance with further characteristics of the invention, the eddy-current probes are spaced from one another by a distance that is substantially less than the diameter of the ferrite cores, and the axes of the coils of the eddy-current probes extend at right angles to the workpiece surface. As a result, an areal high-intensity induction field builds up under the test head which loses but little in intensity between adjacent eddy-current probes so that longitudinal and transverse flaws of the workpiece surface are indicated with maximum accuracy.

The test head in accordance with the invention is preferably made of brass.

The foregoing summary of the invention will become more apparent from the following more detailed description and appended drawings.

DETAILED DESCRIPTION OF THE INVENTION

Figure 1:
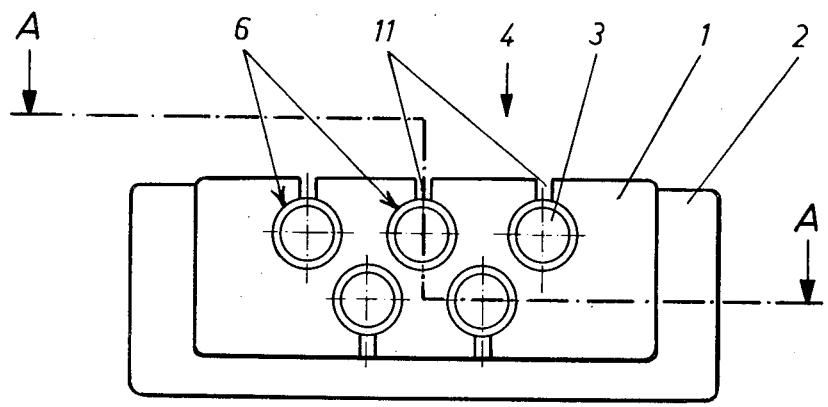
FIG. 1 is a view of the front of a test head in accordance with the invention facing the workpiece.
Figure 2:
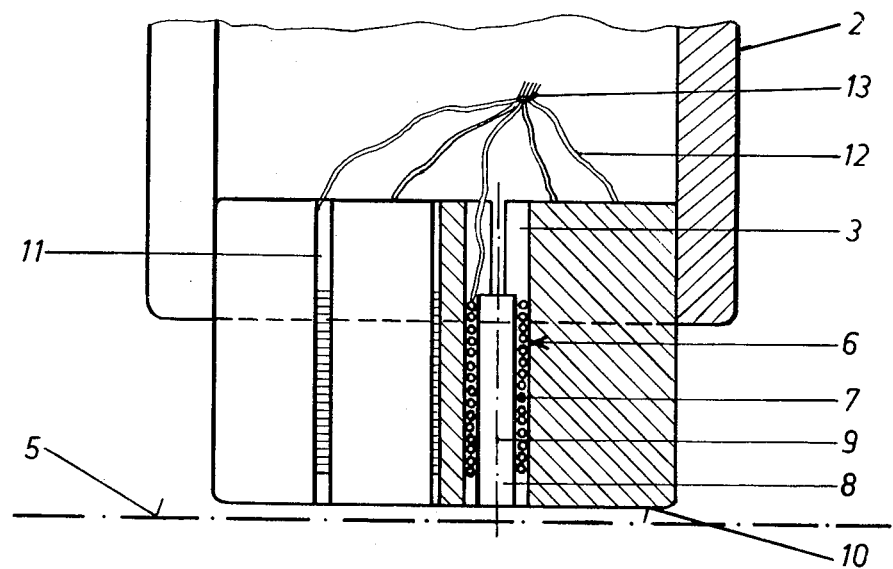
FIG. 2 is a partial longitudinal section through the test head shown in FIG. 1, taken along the line A—A.

In FIGS. 1 and 2, 1 designates a holder made of electrically conducting brass which is secured to a plastic mount 2. The holder 1 has five cylindrical holes 3, disposed at right angles to the direction of movement (see arrow 4) of the surface 5 (shown in FIG. 2 by a dash-dotted line) of the workpiece to be investigated. Set into each hole 3 is an eddy-current probe 6 which is part of an individual resonant circuit. Each eddy-current probe 6 has a single-layer coil 7 with a ferrite core 8, the axis 9 of the coil extending at right angles to the surface 5 of the workpiece.

The ends of the ferrite cores 8 which face the workpiece and the front of the holder 1 which faces the workpiece are in a common plane 10 which is spaced a small distance from the surface 5 of the workpiece. After the coils 7 with the ferrite core 8 have been embedded in the holes 3 by cementing, for example, the surface 10 is advantageously surface ground.

The holder 1 has slotlike notches 11 which extend at right angles to the surface 5 of the workpiece and in the direction of movement of the surface 5 relative to the holder 1. Each of the notches 11 merge into a cylindrical hole 3 accommodating one of the eddy-current probes 6.

The eddy-current probes are spaced from one another by a distance smaller than the diameter of the ferrite cores, which may be as small as 0.8 mm. Moreover, the eddy-current probes 6 are arranged in a zigzag pattern at right angles to the direction of movement (see arrow 4) so that the entire workpiece surface 5 is scanned and tested areally even though the eddy-current probes 6 set into the holder 1 are point-shaped.

The individual eddy-current probes preferably have a resonant frequency approximately equal to the test frequency. They may be operated also in pairs, in a manner not novel in itself (in a differential circuit with a bridge circuit between two coils), and be provided with individual amplifiers.

FIG. 2, the cables 12 of the individual coils 7 are brought out upwardly of the holes 3 and are connected to a soldering terminal 13 on the mount 2.

The test head in accordance with the invention offers the substantial advantage of having, through areal scanning of the workpiece surface, a high indicating accuracy for longitudinal and transverse defects without having to be moved back and forth also in the transverse direction.

The embodiment of a test head in accordance with the invention described above may be modified in a manner consistent with the spirit and scope of the concept underlying the invention. Thus, the coils of the eddy-current probes may also have multiple layers. And instead of being made of brass, the holder may be made of other electrically and/or magnetically conducting materials, such as an anti-friction-bearing steel, which has the desired attenutating effect on the individual resonant circuits. The holder, moreover, may be adapted to the material of the particular workpiece which may also be an antifriction-bearing steel, with resultant insensitivity of the indication to approaching and withdrawing movements of the workpiece surface.

What is claimed is:

1. A test head for the inductive surface testing of metallic workpieces brought into proximity with said test head for areal scanning of the surface of such workpieces, comprising a holder of an electrically conductive material, a plurality of parallel spaced holes extending through said holder, a plurality of resonant circuits each including a coil having a ferrite core and each of said plurality of resonant circuits being mounted in each of said holes and coaxially therewith so that the axes of said coils extend at right angles to the workpiece surface, whereby the resonant frequencies are increased, thereby increasing sensitivity of said testing, the distance between adjacent said holes in said holder being less than the diameter of each said ferrite core so that the magnetic field built up under the test head loses little in intensity between adjacent holes, thereby maximizing accuracy in indicating longitudinal and transverse flaws of the workpiece surface.

2. The test head of claim 1, wherein said holder is made of brass.

3. The test head of claim 1, wherein said holder is made of an antifriction bearing steel.

4. The test head of claim 1, wherein the ends of said ferrite cores facing said workpiece, and the front of said holder facing said workpiece, are disposed in a common plane.

5. The test head of claim 1, said holder being provided adjacent said eddy-current probes, with slot like notches extending at right angles to said surface of said workpiece.

6. A test head as defined in claim 5, wherein said notches extend in the direction of movement of said workpiece surface relative to the holder.

7. A test head as defined in claim 5, wherein said notches merge into the respective holes accommodating the eddy-current probes.

* * * * *